United States Patent [19]

Nicholson et al.

[11] 4,417,662

[45] Nov. 29, 1983

[54] VIAL INSPECTION MACHINE

[75] Inventors: David W. Nicholson, Indianapolis; Larry G. Smith, Plainfield; Harold B. Dinius, Mooresville; Ronald R. Oberle, Indianapolis, all of Ind.

[73] Assignee: Eli Lilly and Company, Indianapolis, Ind.

[21] Appl. No.: 260,003

[22] Filed: May 4, 1981

[51] Int. Cl.$^3$ .............................................. B07C 5/02
[52] U.S. Cl. .................................. 209/522; 209/538; 209/936; 209/938
[58] Field of Search ............... 209/524, 525, 526, 587, 209/588, 905, 704, 538, 522, 523, 702, 938, 936; 250/223 B; 356/427, 428, 240

[56] References Cited

U.S. PATENT DOCUMENTS

| | | |
|---|---|---|
| 1,744,313 | 1/1930 | Kadow . |
| 2,132,447 | 10/1938 | Stout . |
| 2,265,037 | 12/1941 | Gulliksen . |
| 2,531,529 | 11/1950 | Price . |
| 3,097,743 | 7/1963 | Scholten et al. . |
| 3,637,074 | 1/1972 | Banyas ................. 209/905 |
| 3,765,533 | 10/1973 | Stephens et al. ............ 209/524 X |
| 4,234,538 | 11/1980 | Ginsberg et al. ................. 356/435 |
| 4,241,256 | 12/1980 | Tagaya ........................... 356/240 X |
| 4,274,745 | 6/1981 | Takahashi ...................... 356/240 X |

OTHER PUBLICATIONS

Promotional Pamphlet of the Lasko Co.; "Autoskan" Automatic Parenteral Solution Container Inspection Machine; 1975.

Promotional Literature of Robert Seidenader, on Its Inspection Machines "FKM".

Primary Examiner—Robert B. Reeves
Assistant Examiner—Donald Hajec
Attorney, Agent, or Firm—Barnes & Thornburg

[57] ABSTRACT

A continuous series of vials carried by their caps on reciprocable vacuum chucks on a turret move continuously (a) through a gross visual inspection station while slowly rotated and under side, top, and back lighting, and with each vial in an intense beam of light from below which moves with the vial; (b) then, while raised into stabilizing cups, across a spinner belt which rotates the cups and vials at high speed; and (c) then, while stopped with their contents rotating, through a particulate visual inspection station with similar lighting for observation of foreign matter suspended in the contents. Inspectors have unrestricted view of each entire vial, except only for the top of the cap, in a continuous series for comparison or pattern inspection and can, with a finger, tap defective vials off the chucks to a reject conveyor for reinspection. The vacuum chucks are on spindles which are biased upward against a fixed cam which lowers them for pickup, positions them for gross inspection, raises them into the stabilizing spinner cups, and lowers them for particulate inspection and delivery. The turret is vertically adjustable to position the chucks for different bottle heights. The intense bottom light beams which move with the vials are transmitted from fixed light sources through separate fiber optic bundles with their outer ends fixed in a light wheel which rotates with the turret. Polarized back light may be used to enhance inspection for particular purposes as desired.

57 Claims, 10 Drawing Figures

VIAL INSPECTION MACHINE

This invention relates to inspection apparatus, more particularly to apparatus which is especially adapted for the inspection of medicinal vials filled with multiple-dose quantities of a medicinal solution or suspension adapted for parenteral or hypodermic administration and closed by a stopper adapted to be punctured by a hypodermic needle for withdrawal of individual doses; but the inventive concepts are also applicable to the inspection of various other containers and objects.

Medicinal vials should be thoroughly and individually inspected after they have been filled and sealed, and before they are labelled and packaged, to be sure they are free of a variety of possible defects. The vials may have been fed to a filling line directly from the containers in which they were received from a supplier, and in such filling line subjected to various mechanical operations, including, for example, preliminary cleaning such as washing and drying, one or more mechanical filling operations, mechanical closing and sealing operations involving the insertion of stoppers and the application of stopper retainers or covers, and various handling operations, as on mechanical conveyors, in the course of and between these functional operations, before being delivered for labelling and packaging. At the end of such operations, various defects can be present, and a thorough final inspection is necessary before the containers are released for labelling and packaging in preparation for distribution. Such defects may include both functional and cosmetic defects. The defects may include cracked, broken, or misshapen bottles, defective or improperly applied stoppers or stopper covers, incomplete or excess filling, the presence of foreign particles or matter in the bottle contents, etc. Cosmetic defects may include scratches on the bottle, surface dirt, etc. Many of these defects can be readily observed by visual or gross examination if the vial is properly presented to the eye under suitable illumination, but many are difficult to detect. Some defects require special treatment, such as agitation of the vials to cause heavy particles to be suspended in the liquid for observation.

The necessary final inspection has been carried out manually, but this requires manual handling of the vials, and close and concentrated attention from the inspectors over prolonged periods. Various proposals have been made for mechanically and/or optically performing or assisting in the inspection of such vials, but these proposals have heretofore been insufficient or slow or both, and human visual inspection for at least some defects is desirable if the necessary thorough inspection is to be accomplished.

It is the object of the present invention to provide a machine for and method of presenting a continuous series of filled and closed vials for visual inspection by one or two human inspectors, in such a way that a complete and individual inspection of each bottle is accomplished rapidly, with results at least equivalent to those accomplished by manual inspection methods, and thus to provide means which permits the work of eight or nine manual inspectors to be accomplished by only three or four persons. The results of tests with a machine of the type here disclosed have given results as good as or better than the traditional manual method.

In accordance with the best mode of carrying out the invention as presently perceived, a continuous series of objects to be inspected, for example, filled and closed vials, are delivered from a filling line on a conveyor, are individually picked up by their upper ends by a continuous series of axially and rotatably movable chucks, and are carried in suspended position below such chucks sequentially and with continuous travel through a first inspection station at which the vials are preferably in most cases slowly rotated, and where they are lighted with top, side, and back lighting and also with intense beams of light which are directed upward from below onto the bottoms of the several vials and which move with the vials as they travel through the inspection station. The vial-carrying chucks are desirably fluid pressure actuated chucks, such as vacuum chucks, which engage only the top end faces of the caps of the closed vials so that all of the other surfaces are entirely exposed and illuminated both externally by the general lighting and both externally and internally by the intense beams of bottom light which move with the vials.

This permits a visual inspection which is highly effective for detecting substantially all of the defects mentioned above, with the possible exception of foreign matter in the vial contents and especially foreign particles which settle to the bottoms of the vials and must be agitated and suspended in such contents for effective observation.

Inspection for foreign particles is especially desirable and effective with vials containing transparent medicinal solutions. For this purpose, the vials carried in suspended position from the axially and rotatably movable chucks, after passing through the first inspection station, are then rotated at high speeds, for example, 500 rpm, for a time sufficient to cause the liquid contents of the vials to attain a rapid rotative movement. This is desirably accomplished by raising the vials into stabilized relation within spinner cups surrounding the chuck spindles, and rotatably driving such cups as they continuously travel from the first inspection to a second inspection station, as by a belt which engages the stabilizing cups as they are carried through a spinning stage of travel. At the end of the spinning stage, the spinning drive is discontinued, and the chucks and their suspended vials are stopped from rotating and are carried through the second inspection station. Whereas the vial rotation is stopped, the liquid contents of the vials continue to rotate within the non-rotating vials, and this causes foreign particles to be suspended in the liquid so as to be observable at such inspection station, and especially so under the intense bottom lighting from the light beams which move with the vials as they pass through such second inspection station.

At each inspection station, the vials travel across an inspection window in a continuous and continuously moving series so that the inspector can observe each vial over an extended time period. Also, a sufficient number of vials are exposed simultaneously in the inspection window to permit the inspector to compare the several vials each with the others and can observe any departure of one or more vials from the pattern of all those being inspected. Such pattern inspection enhances the individual inspection and is an improvement over manual inspection of separate individual vials.

The rapid rotation of the suspended vials may also be used to mix the contents of the vials, as when they have been filled with a plurality of materials which require mixing, and the spinning drive may be used for this purpose whether or not it is also used or required for purposes of observing foreign particles in the vial contents. When the vial contents are only translucent or otherwise non-transparent, suspended particles are difficult to observe, and in such case, the spinning step and second inspection may be omitted.

The spinner cups which are used to transmit the spinning drive to the vial chucks during the spinning stage are desirably also used to rotate or control the rotation of the vial chucks at other stages, as by the use of a belt to effect slow rotation of the chucks and vials during their travel through the first inspection station.

A machine for carrying out the inspection procedures outlined above desirably comprises a wheel or turret rotatable on a vertical axis and carrying at its periphery a circumferential series of vertically and rotatably movable spindles having chucks at their lower ends and vertically positioned at desirable elevations by cam means disposed about the axis of the turret. The preferred vacuum chucks may be connected by passages in the spindles to a manifold which supplies vacuum to the chucks over a predetermined travel of the chucks about the turret axis, and which may be connected to a source of air under pressure at a vial delivery position to positively remove the vials from the chucks at that position. A continuous series of vials may be supplied to the chucks from a supply conveyor by means of infeed means such as an infeed star wheel synchronized with movement of the turret, and the inspected vials may be discharged from the turret and its chucks to a delivery conveyor by outfeed means such as an outfeed star wheel.

Any vial which is found defective for any reason during the inspection may be removed by the inspector by lightly tapping the vial with a finger to dislodge it from its vacuum chuck and cause it to fall inward onto a reject collection plate from which sweep arms carry it to a delivery chute and reject conveyor leading to a manual reinspection station.

The beams of intense bottom light which move with the vials as they travel through their inspection path are desirably provided by a series of light-transmitting means, such as fiber optic bundles which have their discharge ends fixed in a light wheel below the path of the vials and movable with the turret so that such discharge ends remain in alignment with the bottoms of such vials throughout their travel through the inspection machine. The optic bundles desirably extend inward, as through the reject sweep arms which form spokes from the rim of the light wheel, toward the central axis of the turret, and their input ends are positioned to travel across one or more sources of intense light so located as to provide intense light to such fiber bundles as their output ends travel across the two inspection stations.

Side, top, and back lighting for the vials may be provided at the inspection station by light boxes which include a translucent back-light panel lighted from behind by incandescent light, and one or more overhead fluorescent light tubes. Such light boxes, mounted inside the path of the revolving continuous series of chuck spindles and chuck-supported vials may be supported by supports which extend through such path at clearance positions, such as between the outfeed and infeed star wheels where the chucks carry no vials, and at the position where the chucks are raised to lift the vials into the stabilizing cups for spinning.

To adapt the inspection machine for the inspection of different vials, the means which carries the several spindle asemblies is vertically adjustable relative to the elevation of the input and output star wheels and the light wheel. To this end, a chuck carrier or turret may be vertically positioned by a thrust bearing in a top cross head which is vertically adjustable with respect to the base of the machine on which the star wheels are mounted. To accommodate bottles of different diameters or shapes, the infeed and outfeed mechanism may have change parts, and the spinner cups may have replaceable inserts to fit the different vials.

The accompanying drawings illustrate the invention, and show an embodiment exemplifying the best mode of carrying out the invention as presently perceived. In such drawings.

Figures 1, 2, 3:
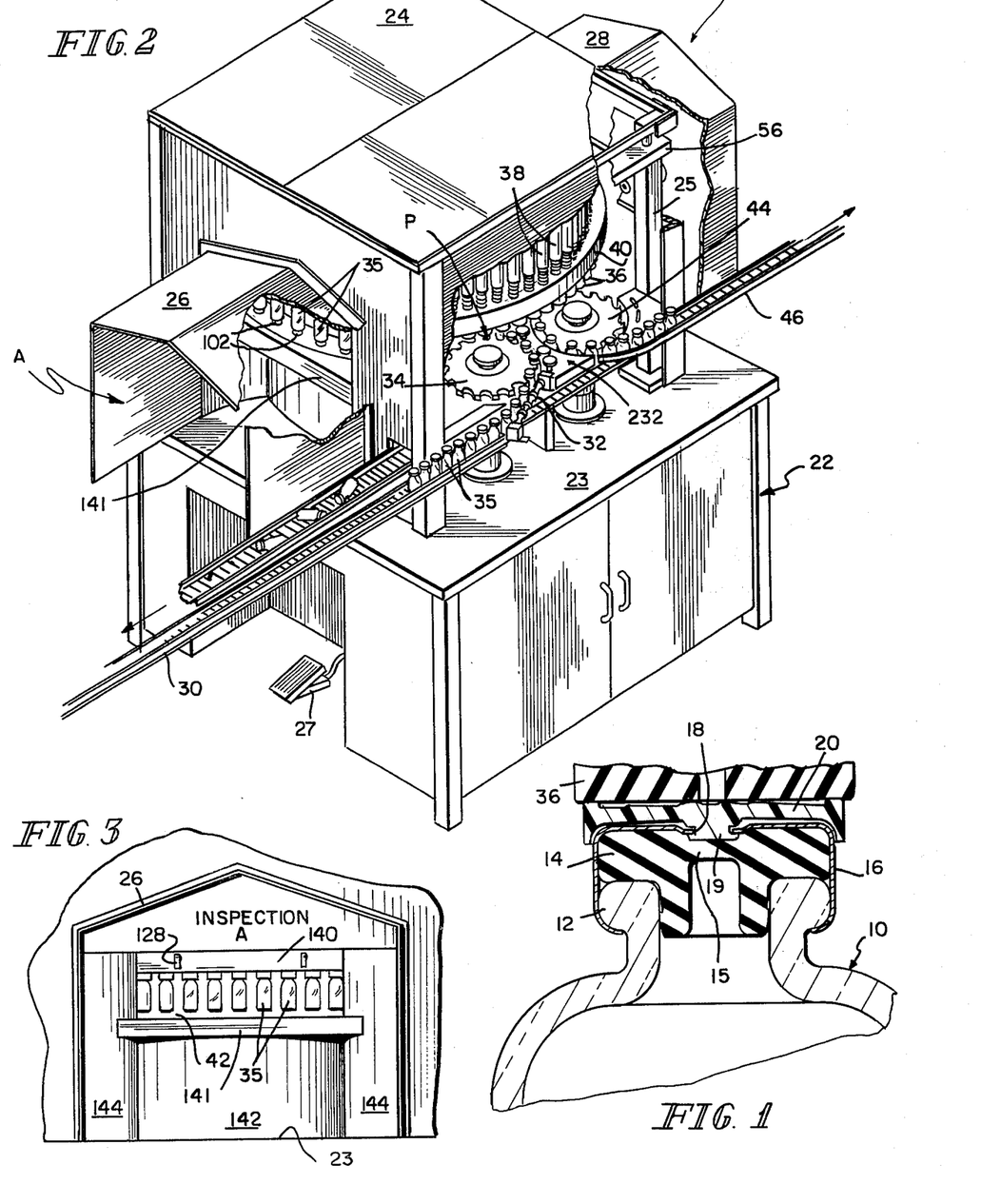
FIG. 1 is a vertical section showing the upper end and the closure of a vial of a type which the disclosed embodiment is especially adapted to inspect.
FIG. 2 is a general perspective view of an inspection machine in accordance with the present invention and provided with two inspection stations.
FIG. 3 is an elevational view looking into the first inspection station.

The inspection machine shown in the drawings is especially adapted for the inspection of filled and closed medicinal bottles or vials as shown in FIG. 1. The vial shown comprises a small bottle 10 having a beaded neck 12 closed by a puncturable rubber stopper 14 having a central area 15 adapted to be repeatedly punctured by a hypodermic needle for the withdrawal of single doses of the multiple-dose quantity of medicinal liquid contained in the vial. The stopper 14 is secured in place against the end face of the beaded neck 12 by a metal cup or cover 16 which is crimped at its bottom edges beneath the bead on the neck. The cover top wall has a central section 18 overlying the puncturable section 15 of the stopper, defined by a weakened break line and engaged about a stud 19 on a cap 20. The cover 16 and stud 19 of the cap 20 completely overlie the end face of the stopper to protect it until the vial is to be used. When the vial is to be used, the user lifts the edge of the cap 20 so as to break away the central section 18 of the top wall of the cover and expose the central puncturable portion 15 of the stopper. For present inspection purposes, it is to be noted that the cap has a top surface which includes a continuous rim and is adapted to be held by a vacuum chuck 36 engaged against such top surface. On the one hand, the cap 20 must remain in place during the inspection but, on the other, must be readily removable by the user, and hence the inspection operation must be such that it does not impose undue stress on the cap or cover. It is found, however, that vials closed with such stoppers and covers and caps readily withstand the stresses imposed by the inspection handling in the present machine, and that the caps 20 are not broken away by the manual force required to dislodge defective vials from the vacuum chucks which carry them through the inspection machine.

The inspection machine shown in FIG. 2 comprises an enclosed base cabinet 22 which houses drive mechanism and controls for the operating parts of the machine and which provides a top base plate 23 having a flat surface which can be fully exposed during changeover from the inspection of one vial product to another so as to avoid the danger that vials containing the one product can become mixed with vials containing the other product.

A housing 24 is mounted by corner posts 25 on the base 22. The housing carries a hood 26 for defining and shrouding a first inspection station A on one side of the housing 24 and a hood 28 on the other side of the housing for defining and shrouding a second inspection station B. An infeed conveyor 30 supplies a continuous line of vials 35 to an infeed worm 32 which leads to an infeed star wheel 34 that moves the vials in timed sequence to a pickup position P below a series of chucks 36 carried by a series of spindle assemblies 38 on a turret 40. As more fully explained below, the chucks 36 moving with the turret carry the vials 35 in a continuously moving series, first across the inspection station A and later across the inspection station B, and then deliver them to the outfeed star wheel 44 which delivers them to an outfeed conveyor 46 which may be a continuation of the infeed conveyor 30.

To define and shroud the inspection station, each hood 26 and 28 comprises top and side walls adapted to receive the head and shoulders of an inspector who is positioned within easy reach of the vials moving across the inspection station. An inspection window 42 is defined at each station at the top by an upper shield 140, at the bottom by a cross bar 141 and an arcuate shield 142, and at the sides by side shields 144. Desirably, the bottom shield 142 and the side shields 144 are readily removable to expose the surface of the base plate 23 for cleaning and examination for any loose vials. Each inspection station has a foot switch 27 for controlling machine operation. The width of the window is sufficient to expose a number of the closely spaced vials to permit comparative or pattern inspection. Such number may vary with different objects being inspected, and for simple vials such number is preferably at least about five. In the embodiment shown, nine such vials are simultaneously exposed, and we find that number to be sufficient.

Figure 5:
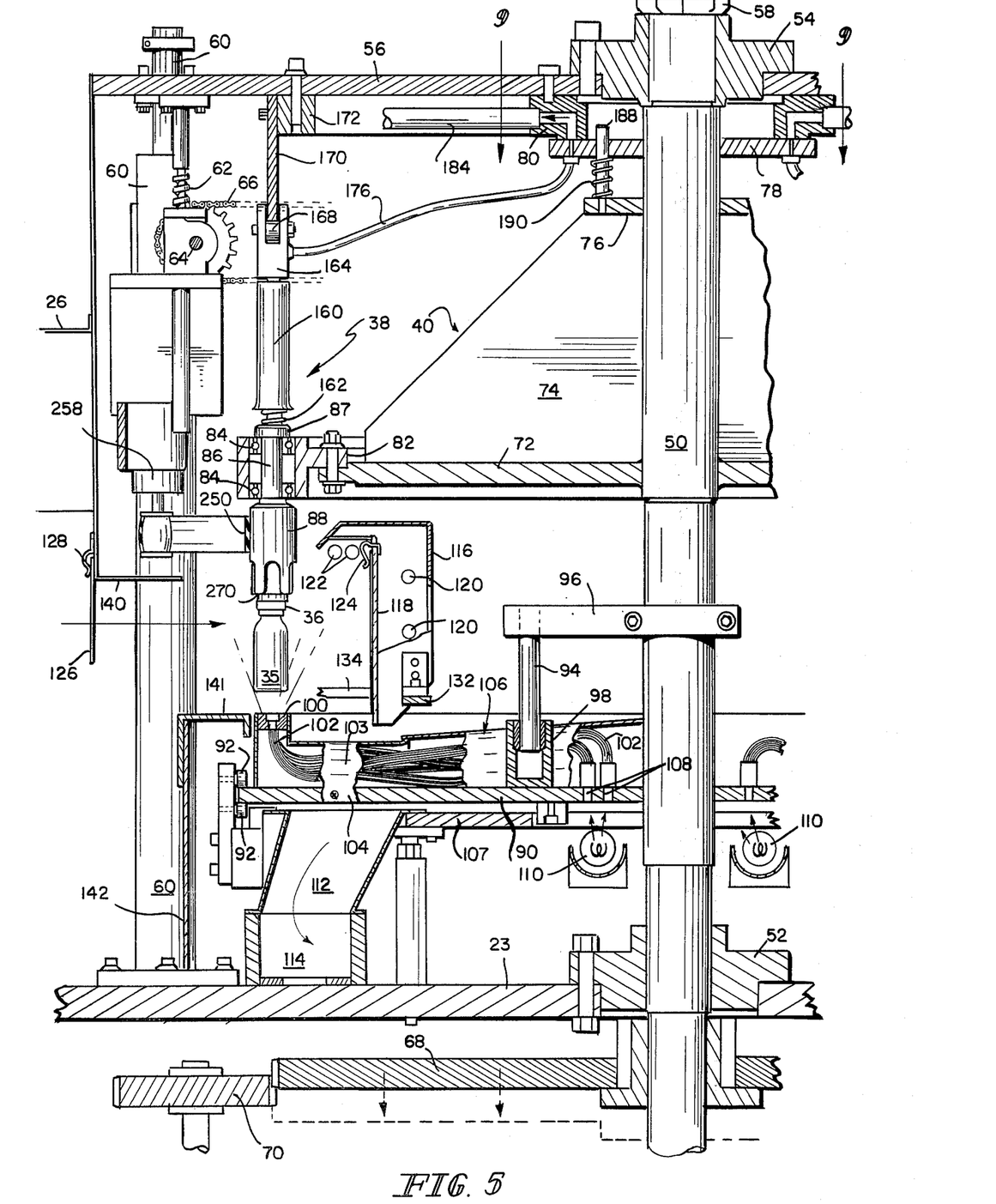
FIG. 5 is a vertical sectional view, taken generally on the line 5—5 of FIG. 4, but with certain parts, such as the reject vial chute and conveyor, moved into that plane for convenience of illustration.

The inspection machine, as viewed in vertical section, FIG. 5, comprises a central turret shaft 50 mounted for rotation and limited vertical adjustment in a lower bearing 52 in the base plate 23 forming the top of the base cabinet 22, and mounted for rotation in an upper bearing 54 carried by a plate-like cross head 56 at the top of the machine. The weight of the shaft is carried, and its vertical position is determined by a thrust collar 58 bearing against the upper end of the bearing 54. The cross head 56 is mounted for vertical slidable adjustment on four corner posts 60, and is arranged to be raised or lowered thereon by screw jacks 62. The two screw jacks 62 at each side of the machine are interconnected by shafts 64, and the two pairs of shaft-connected jacks 62 are interconnected by a chain 66, so that the four screw jacks 62 will operate together to raise and lower the cross head 56. The column 50 carries a large drive gear 68 below the base plate 23, arranged to be driven by a spur gear 70. These two gears have wide faces, so that they remain in mesh over a considerable range of vertical adjustment of the shaft 50 and permit such adjustment without loss of drive to the column 50. As shown in FIG. 5, the turret is in substantially its uppermost position of adjustment.

The turret 40 includes a spindle carrier plate 72 fixed to the column 50 intermediate its height and reinforced with a plurality of angularly spaced radial ribs 74 fixed to the shaft 50 and at their upper edges to a smaller disk 76. Above such disk 76, the shaft 50 carries a vertically slidable manifold valve plate 78 which bears against an annular manifold 80 carried by the cross head 56, for purposes to be described more fully in connection with FIG. 9. The spindle carrier plate 72 on column 50 is connected at its outer edge to a circular rim 82 which carries the outer races of a plurality of pairs of ball bearings 84 in which are mounted the stems 86 of a plurality of spinner cups 88. Such stems and cups form parts of the spindle assemblies 38 for the vacuum chucks 36 on which the vials are carried through the inspection sequence, as will be more fully described in connection with FIGS. 6 and 7. As seen in FIG. 5, the vial chucks 36 are adapted to support vials 35 in an inspection position shown in full lines in this figure.

In a position spaced well below the spindle carrier plate 72 and below the vials 35 carried by the chucks thereon, the column 50 is surrounded by a light wheel 90 of circular shape which is supported for rotation in its plane by a plurality of pairs of rollers 92 spaced about its periphery and supported from the base plate 23. The light wheel 90 is driven by a drive pin 94 carried by a bracket 96 fixed to the shaft 50 and slidably received in a drive cup 98 fixed to the light wheel at a point spaced outward from its inner periphery. The light wheel 90 carries adjacent its periphery a light rim 100 in which are fixed the outer or discharge ends of a plurality of light-transmitting elements, preferably fiber optic bundles 102, at points spaced below and in alignment with the axes of the vials 35 carried by the spindle assemblies 38. The light-transmitting bundles 102 extend inward from the light rim 100 through housings 103 on spoke-like arms 104 to an annular space between the inner portion of the wheel disk 90 and an overlying shroud 106. Within this space, the inner ends of the optic fiber bundles 102 are fixed in an annular series of holes 108 in the light wheel which, during rotation of the light wheel, travel across an intense light source assembly comprising a plurality of lamps 110. Such light source assembly supplies light to the inner ends of the fiber optic bundles as their outer ends travel past the inspection stations A and B, or past whichever one of such inspection stations is being used.

An annular vial reject collection plate 107 is mounted in fixed position closely below the spoke-like arms 104. Defective vials observed by the inspectors are manually dislodged from their chucks and fall onto such plate, between the spoke-like arms 104 through which the optic fiber bundles extend, and such arms sweep the rejected vials around the surface of underlying plate 107 to a chute 112 leading to a reject conveyor 114 which carries the rejected vials to a reinspection booth, not shown.

For purposes of providing top, side, and back lighting for the vials being inspected, a light box 116 is mounted in the space between the light wheel 90, 100 at the bottom and the spindle carrier plate 72 at the top, at each of the inspection stations. As shown in FIG. 5, the light box 116 comprises a generally closed box-like structure with a translucent plate 118 covering its front face and lighted from behind by incadescent bulbs 120. A hood at the top of the box projects forward and supports a pair of fluorescent tubes 122 well above the inspection position of vials as shown in FIG. 5. The upper edge of the translucent plate 118 desirably carries a plurality of clips 124 for supporting a filter or light-polarizing screen over the face of the translucent plate 118. A companion screen support is formed by the front face of the shield 140 at the top of the inspection window. The second screen will thus be located outside the path of the vials 35 and sufficiently spaced from the vials being inspected to allow the operator to reach behind the screen to dislodge vials to the reject-receiving plate. A plurality of clips 128 are mounted on such face for securing the second filter or polarizing sheet at that position. Inspection for certain defects is enhanced by using a polarizing sheet which polarizes the back light in one plane behind the vials and a second sheet which polarizes the light in a different plane in front of the vials so that background light is subdued while light scattered by such defects is relatively enhanced. Such screens are especially useful for inspecting for particulate matter at the second inspection station B, but are here shown at the first station A.

Figure 4:
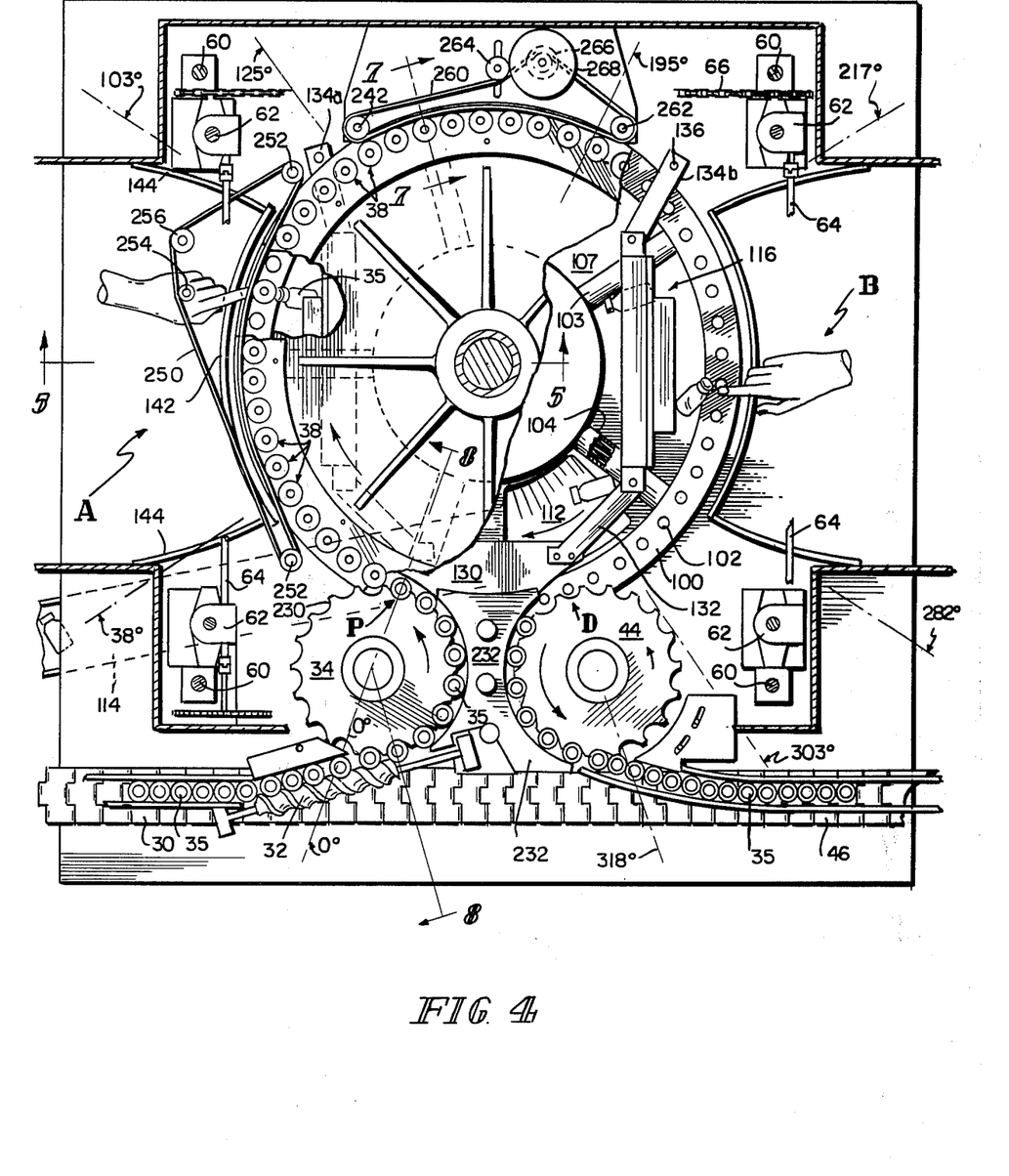
FIG. 4 is a horizontal plan or layout view of the machine of FIG. 2 with the upper housing and carrier plate removed and with parts broken away to show the mechanism at different elevations.

The light boxes 116 lie within the circular path of the vials carried by the chuck spindle assemblies, and between structures which are rotating during operation, so that special provisions for their support must be provided. As shown in FIG. 4, a support plate 130 is mounted between the infeed star wheel 34 and the outfeed star wheel 44 and extends across the rim 100 of the light wheel 90 to a position inside such light rim 100 and inside the circular path of the vials being inspected. A bracket 132 mounted on such support plate 130 supports the adjacent end of each light box 116. The opposite end of each light box carries a bracket connected to a mounting arm 134 which extends across the light rim 100 at a position where the vials 35 are elevated into the spinner cups 88 so as to provide clearance between such light rim and the elevated vials for such passage. The outer end of the support arm 134 is fixed to a post 136 mounted on the base plate 23 of the machine.

Figure 6:
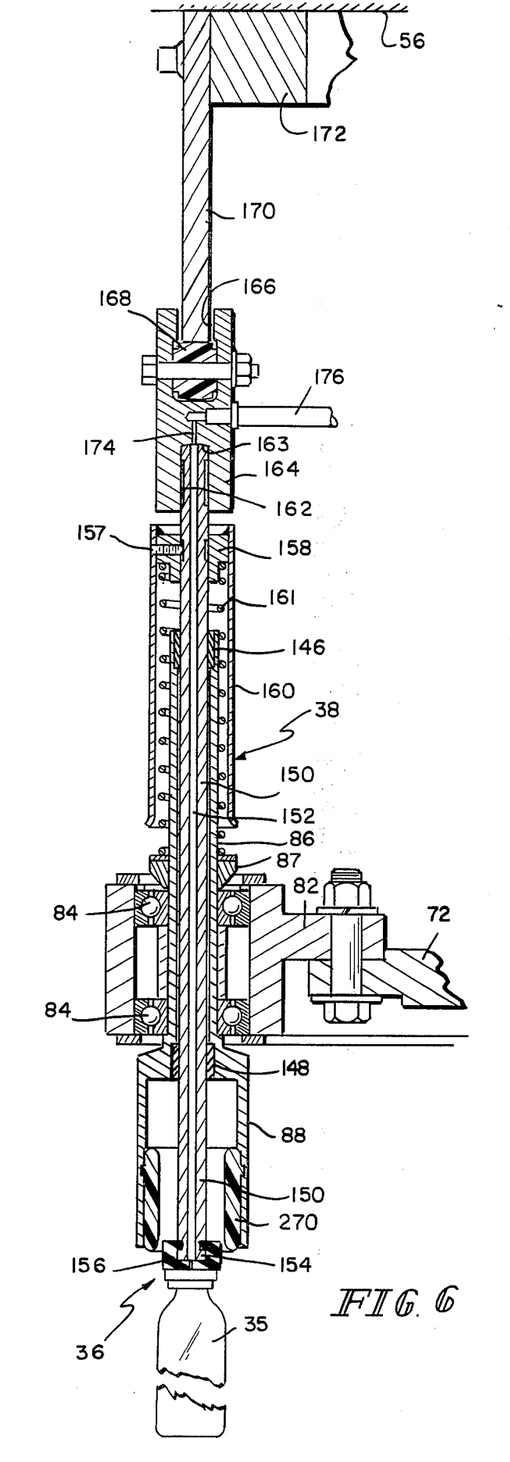
FIG. 6 is an enlarged vertical section showing the chuck spindle and stabilizing cup assembly and its mounting, with the chuck in a lowered inspection position.
Figure 7:
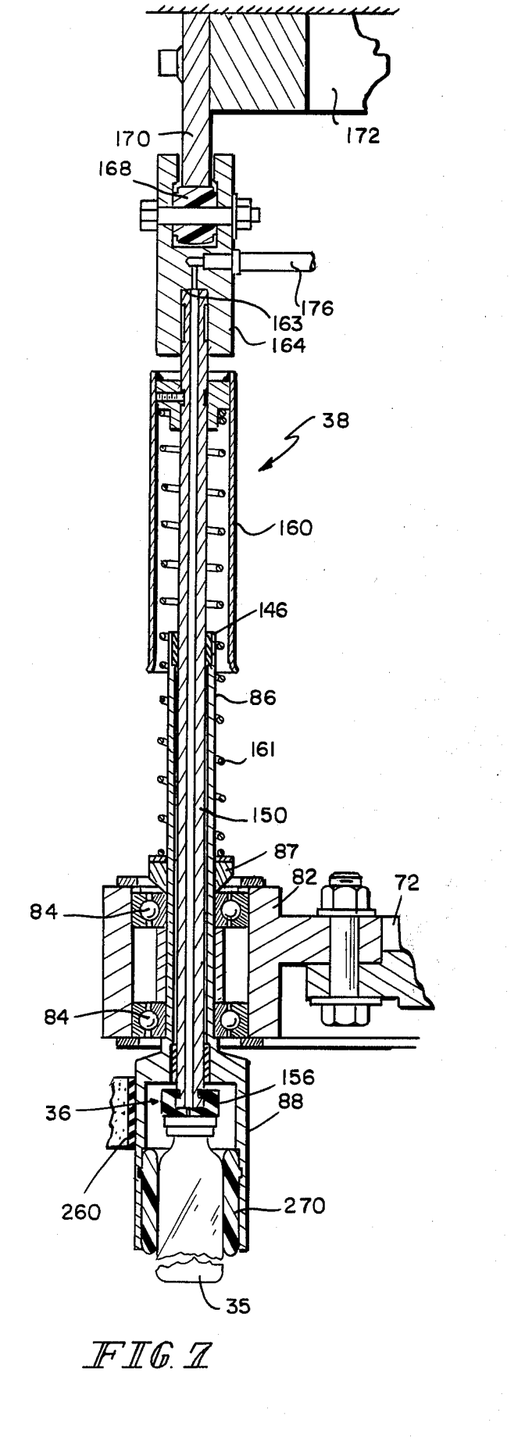
FIG. 7 is a sectional view like FIG. 6, but with the chuck and its spindle in elevated position to locate the vial within the stabilizing cup, taken on the line 7—7 of FIG. 4.

The spindle assemblies 38, best shown in FIGS. 6 and 7, comprise the spinner cups 88 and their stems 86 by which they are mounted in the bearings 84 in the peripheral ring 82 of the turret. The stems are fixed in the bearings by a bottom shoulder and a top collar 87, and the bearings support the spinner cups for free rotation at a fixed elevation just below such ring 82. The stems 86 extend upward a considerable distance above the ring 82 and are provided at their ends with upper and lower bushings 146 and 148. A hollow chuck spindle 150 having a central passage 152 along its axis is mounted in such bushings. The lower end of the spindle is formed with a head 154 which carries a soft elastomer disk 156 having a central orifice. The bottom face of such disk is adapted to make sealing engagement with the cap of a vial 35 so that when the central passage 152 of the chuck spindle 150 is under reduced air pressure, such disk 156 forms a vacuum chuck 36 for supporting the vial 35.

The upper end of the spindle 150 extends beyond the stem 86 of the spinner cup and adjacent its upper end is fixed in thrust-transmitting relation with a collar 158, as by a set screw 157. The collar carries a depending outer sleeve 160, and a compression spring within such sleeve extends between the collar 158 and the bearing collar 87 so as to urge the chuck spindle 150 upward. The top end of the spindle 150 is received in a socket 162 in a cam follower 164. The cam follower is desirably formed as a block of plastics material having low-friction bearing characteristics, and the inner end of the socket 162 forms a thrust bearing 163 riding against the end surface of the spindle 150. The upper portion of the cam follower is formed with a central slot 166 to receive the bottom edge of a cam 170, and a cam follower roller 168 is mounted in the bottom of such slot 166. The cam 170 is in the form of an elongated strip bent in a circle to conform with the circular path of the spindle assemblies 38 carried on the turret 40. The cam is conveniently mounted on a rail 172 secured to the cross head 56.

Figure 9:
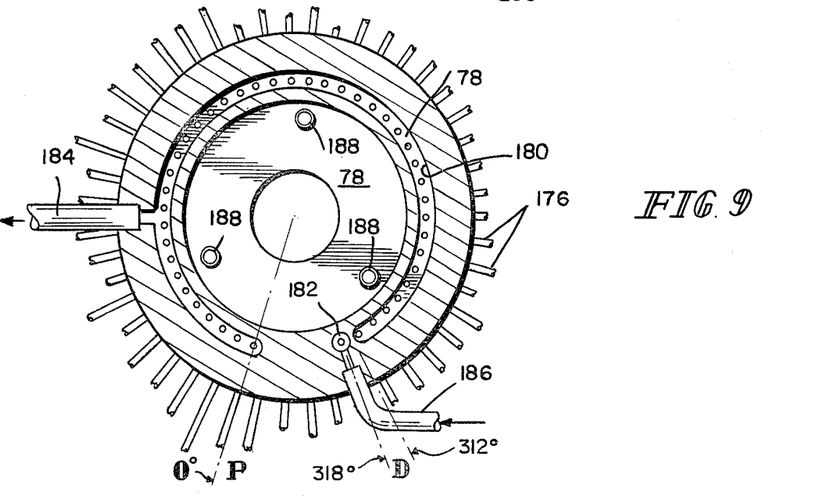
FIG. 9 is a horizontal section, taken generally on the line 9—9 of FIG. 5 showing the vacuum and air pressure manifold.

Each cam follower 164 is formed with an air passage 174 leading from the thrust bearing 163 at the end of the spindle socket 162, for connecting the spindle passage 152 to a vacuum line 176 fixed to the cam follower. As shown in FIGS. 5 and 9, the several vacuum lines 176 are connected to the valve plate 78 adjacent the top of the central column 50 and biased against the face of the manifold 80. Such manifold 80 contains a vacuum chamber 180 which extends from a position P coordinated with the pickup point at which the turret picks up vials from the infeed star wheel 34 through an arc of, say, about 315°, to a point ahead of the point D at which the vials are dropped or discharged from the chucks 36 to the outfeed star wheel 44. At that point D, the manifold 80 contains a small air pressure chamber 182. The vacuum chamber 180 is connected to a vacuum supply line 184, and the air pressure chamber 182 is connected to an air supply line 186. The valve plate 78 is connected to be driven with the column 50 by a series of drive pins 188 carried on the top plate 76 of the turret, and is biased against the face of the manifold 80 by springs 190 engaged about such pins 188. With this arrangement, the chucks 36 are continuously supplied with vacuum from the vial pickup point P throughout their path of travel to a point just short of the vial discharge point D, so as to activate the chucks for holding vials thereon throughout that travel. At the point D of vial discharge to the outfeed star wheel 44, the chucks are supplied with air under pressure so as to positively release the vials from the chucks and allow them to drop into and be carried away by such outfeed star wheel.

Figure 8:
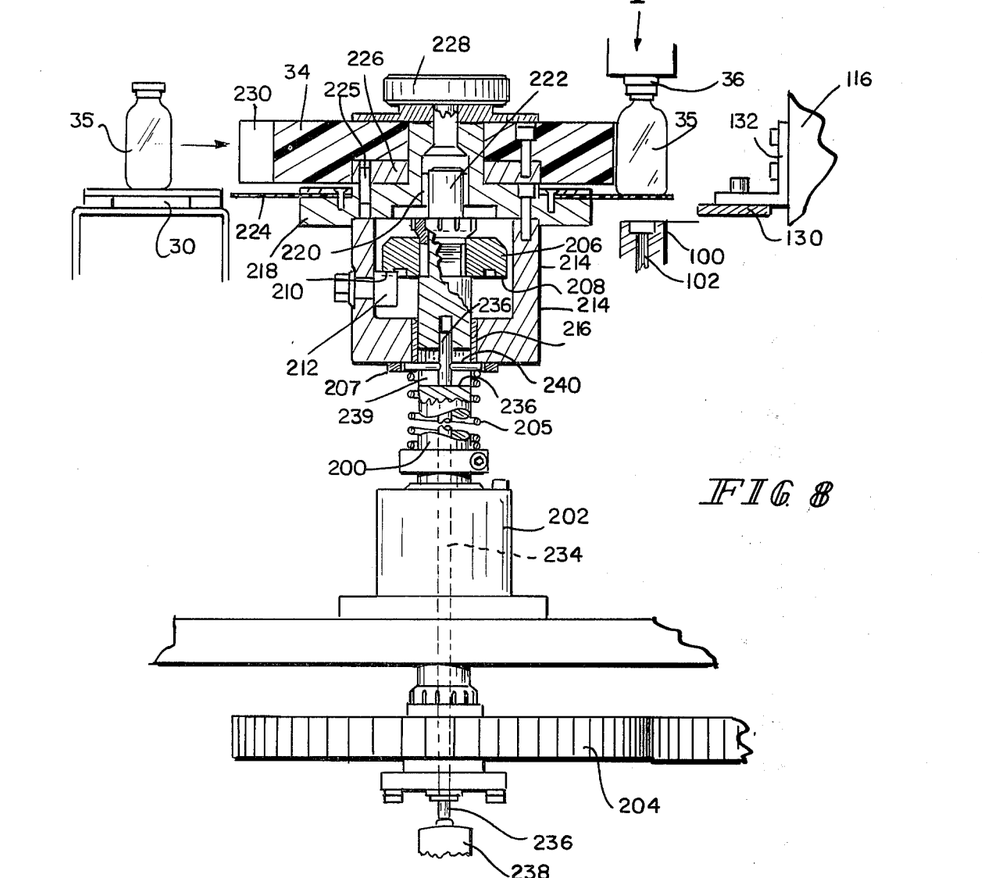
FIG. 8 is a vertical section, taken generally on the line 8—8 of FIG. 4 showing the infeed star wheel and its drive mechanism.

The two star wheels 34 and 44 are desirably replaceable units, and the infeed star wheel 34 is desirably driven by a torque-releasable clutch. The arrangement and drive mechanism of the infeed star wheel are shown in FIG. 8. A vertical star wheel drive shaft 200 is mounted in a bearing block 202 supported on the base plate 23 at the top of the cabinet base 22, and is driven from below by suitable gearing 204. The upper end of the shaft 200 carries a drive collar 206, keyed thereto. The collar has a depending outer rim 208 which is interrupted at angularly spaced points by arcuate notches 210, one of which is normally engaged by a clutch roller 212. The roller 212 is carried by a cup 214 which has a central bottom bearing 216 in rotatable and slidable engagement with the shaft 200. The upper end of the cup is fixed to a carrier plate 218 having a central opening containing a pilot bearing 220 engaged about the reduced top end 222 of the shaft 200. The drive plate 218 carries a thin support plate 224 for supporting vials 35 being fed by the star wheel. The star wheel 34 is a circular wheel, preferably of synthetic plastic material, containing a drive collar 226 and removably received over a central post of the drive plate 218. It is held in place by a hand knob 228 and is drivingly connected to the drive plate 218 by a dowel pin 225. The periphery of the star wheel is formed with a plurality of pockets 230 shaped to receive a series of vials 35 from the infeed conveyor and convey them to the turret 40.

The torque-releasable drive connection between the vertical drive shaft 200 and the star wheel assembly is as follows. The star wheel assembly, including the drive cup 214, the drive plate 218 fixed thereto, and the star wheel 34 removably fixed to that drive plate are biased upward relative to the drive shaft 200 by a spring 205 acting between a collar on the shaft 200 and a thrust washer 207 on the bottom face of the cup 214, and this urges the clutch roller 212 into normal driving engagement with one of the notches 210 in the depending peripheral flange 208 of the drive collar 206 keyed to the shaft 200. This transmits drive from such collar to the star wheel assembly under normal conditions. If the star wheel encounters resistance, as from a bottle becoming jammed between the star wheel and adjacent structure, such resistance will cause the clutch roller 212 to be cammed downward out of the drive notch 210, so as to allow the roller 212 to ride along the bottom face of the depending rim 208 of such collar without transmitting drive to the star wheel assembly. Such downward camming of the roller 212 moves the entire star wheel assembly downward as a unit against the bias of the spring 205, and this has the advantageous result that the downward movement lowers the vials 35 away from the vacuum chucks 36, so that chucks will not pick up any vial 35 which is at or nearly at the normal pickup point.

Desirably, this downward movement also triggers a safety switch to interrupt the operation of the machine. To this end, the drive shaft 200 is formed with a central bore 234 in which is mounted a thrust rod 236 extending downward into operative relation with a safety switch 238 mounted below the gearing 204. To connect such rod 236 to the star wheel assembly, the shaft 200 is also formed with a cross slot 239, and a drive pin 240 is mounted in such slot and through a hole in the thrust rod 236. The pin is trapped in notches in the thrust washer 207 and bears against the bottom face of the cup 214. Accordingly, when the cup 214 is lowered as a result of torque-responsive disengagement of the clutch roller 212 from the drive collar 206, the drive pin 240 transmits such downward movement to the thrust rod 236 and this actuates the safety switch 238 to interrupt the drive.

The outfeed star wheel 44 likewise comprises a removable star wheel element containing peripheral pockets 230 to contain the vials and is held in place by a hand knob 228 so that it can be removed and replaced to adapt the machine for the inspection of different size bottles. The star wheel 44 may have a drive similar to that shown in FIG. 8 for the infeed star wheel 34.

As shown in the sectional view of FIG. 8, the star wheel 34 lies adjacent the infeed conveyor 30 to receive vials 35 therefrom. As shown in FIG. 4, the vials 35 are held in the peripheral pockets 230 by a guide block 232 as they are fed toward the point P at which they are picked up by the chucks 36 of the turret. This position P is shown at the right of FIG. 8, and it is seen that the vial 35 rests on the support plate 224 and that such plate overlies the rim portion 100 of the light wheel which carries the output ends of the several bundles of fiber optic bundles 102 described above. In this position, there is a portion of the mounting plate 130 which lies inward of the peripheral edge of the support plate 224 of the star wheel, and to which position it projects from its support beneath the guide block 232 through the space between the infeed star wheel 34 and the outfeed star wheel 44. It thus projects to within the circular path of the spindle assemblies 38 to provide a mounting base for the support bracket 132 for the adjacent end of a light box 116.

It is desirable to control the rotation of the vials as they are carried through the first inspection station A. To this end, as shown in FIGS. 4 and 5, as the spindle assemblies 38 travel across the first inspection station A, the cylindrical outer surfaces of the spinner cups 88 are engaged by a drive belt 250 stretched over a pair of end pulleys 252, an adjustable idler pulley 254, and a driving pulley 256 driven by a variable speed motor 258. The belt 250 can be driven at various rates relative to the speed of rotation of the turret 34 so as to cause the spinner cups 88 either to remain stationary and thereby carry the vials 35 in pure translation across the inspection station, or to rotate the spinner cups and the vials 35 one way or another at selected speeds during their travel past the inspection station. In usual operation, the belt 250 is preferably driven to cause the vials 35 to be rotated slowly as they travel across the first inspection station.

The second inspection station B may be provided with a similar belt for controlling the rotation of the spinner cups 88 and the vials 35 as they travel across the second inspection station.

For inspecting vials filled with transparent liquid, especially to inspect of the presence of particles therein which may tend to settle to the bottom of the vial, the vials are desirably rotated at high speeds during their travel from one inspection station to the other so as to get both the vial and its contents rotating, and thereby cause such particles to be suspended in the liquid. The vials are then stopped from rotation while the contents continue to rotate during inspection at the second inspection station so that the suspended particles can be observed. For purposes of rapidly rotating the vials in their travel between the two inspection stations, the machine is provided at the rear with a belt 260 stretched about two end pulleys 262, an adjustable idler pulley 264 and a drive pulley 266 driven by a variable speed motor 268. Such belt 260 engages the outer cylindrical surface of the spinner cups 88, as shown in FIG. 7.

In order to stabilize the vials 35 carried by the vacuum chucks 36 during this high-speed rotation, and prevent them from being thrown off the chucks, the vials are desirably elevated during such rotation into the spinner cups where they are closely surrounded by stabilizing inserts 270. As shown in FIG. 7, each spinner cup 88 has a bottom tubular insert 270 of a size to closely surround the vial 35. Such insert is desirably made of soft material and with sufficiently close clearance about the vial 35 to stabilize it substantially on the axis of the spindle 150. Such elevation is effected as the spindle assemblies travel from the first inspection station to the position of the spinner belt 260. To this end, the cam 170 is shaped to allow the biasing spring 162 to move the spindle 150 upward relative to the spinner cup 88 and its stem 86 during such travel, so as to draw the chuck 37 into the spinner cup 88 and elevate the vial 35 carried by such chuck into the stabilizing insert 270. There is some flexibility in the sealing disk 156 which forms a sealing face of the vacuum chuck 36, and the vial 35 need not be exactly symmetrical about the axis of the spindle and some eccentricity can occur as the vial is spun at high speeds, such as 500 rpm. The stabilizing insert 270 holds the vial 35 substantially on the axis of the spindle and prevents it from being thrown off the vacuum chuck 36 while the spinning movement occurs to accelerate the bottle contents to high-speed rotation for subsequent inspection for particulate matter. As the rotating spinner cups are carried past the spinner belt 260, shown at the top of FIG. 4, the frictional drag of the bearings on the rotating spindle assembly is sufficient to stop the rotation of such assembly and the vials carried by the chucks, while leaving the vial contents rotating at high speed. Also, before the spindle assemblies reach the second inspection station B, the cam 170 shown in FIGS. 5 and 10 causes such assemblies to be lowered against their biasing springs 161, to lower the chucks 36 and thereby lower the vials 35 to a position for observation as the vials are carried across the second inspection station B.

In normal operation, the turret 40 is driven at a continuous speed, its spindle assemblies pick up a continuous succession of vials from the infeed star wheel 34 at the pickup point P, and carry them with continuous motion about the circle of movement of such assemblies with the turret, and hence in a continuous, closely spaced sequence successively across the windows of the two inspection stations A and B. At any time an inspector notices a defect in any vial, such inspector simply taps such vial with a finger so as to dislodge it from its vacuum chuck and cause it to fall inward onto the reject-collection panel 107 over which it is swept by the arms 104 of the light wheel to the discharge chute 112 and thence to the reinspection conveyor 114.

Figure 10:
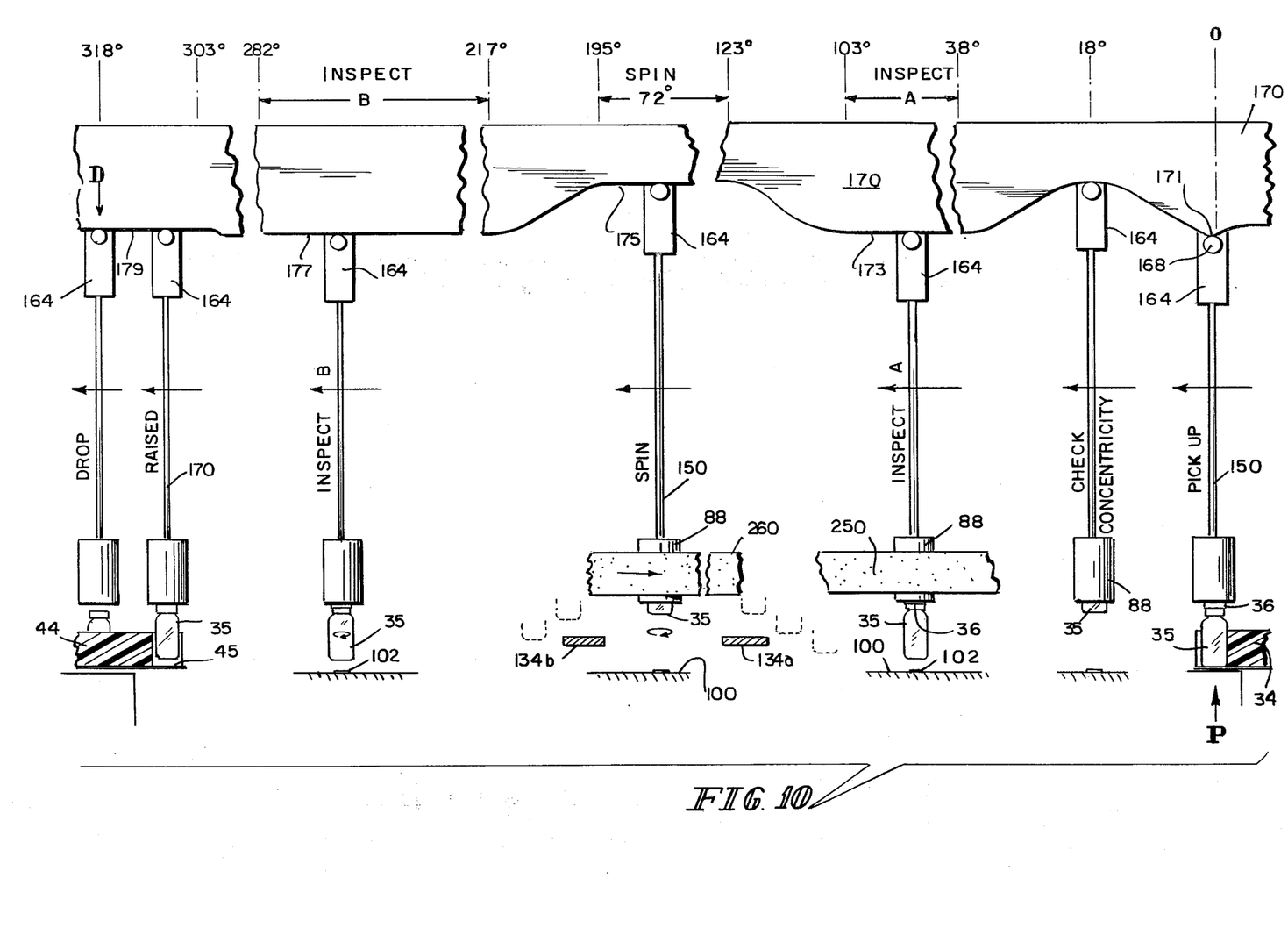
FIG. 10 is a diagrammatic view showing a layout of the spindle control cam and indicating the several steps and stages of operation of the inspection machine of FIG. 2.

The sequence of operation of the inspection machine is indicated by the diagrammatic view of FIG. 10 showing a layout of the cam 170 and showing the positions of a chuck spindle 150 and chuck 36 and vial 35 at successive stages of travel through the machine. On such diagrammatic view of FIG. 10, certain significant positions are indicated in angular degrees, representing angular travel of a particular vial in the machine shown, and this view may be taken in conjuction with the general plan view of FIG. 4 and the manifold plan view of FIG. 9 on which similar significant angular positions are also indicated. In these figures, the starting or zero degree position is arbitrarily taken at the pickup position P at which vials 35 are picked up by the chucks 36. Beginning with that position and proceeding from right to left in FIG. 10, the several operations to which a vial is subjected in the successive stages of the inspection cycle are given below. For purposes of this explanation, it is assumed that the vials being inspected contain a transparent solution and are to be inspected both for gross defects and for the presence of particulate matter.

0 Degree Position

At this position, the cam 170 has a depending nose 171 which, when traversed by the roller 168 of the cam follower 164, depresses that cam follower and the chuck spindle 150 to cause the chuck 36 to be lowered into contact with the top surface of the cap 20 of the vial 35 brought into alignment with the chuck by the infeed star wheel 34. Concurrently, the suction line 176 controlling the vacuum supply for that chuck 36 is connected to the vacuum chamber 180 as indicated in FIG. 9, so that the chuck 36 is activated to pick up the vial 35.

0 Degree to 18 Degrees

During this angular travel, the cam follower 164 rides along a cam rise so that the spindle 150 is lifted by the spring 161 and elevates the vial 35 carried thereby upward into the spinner cup 88. This has the effect of checking the position of the vial 35 with respect to the axis of the chuck and spindle. If the vial 35 is not in proper alignment to enter the insert 270 of the spinner cup as shown in FIG. 7, the vial will be dislodged from the chuck and will normally fall inward onto the reject-collection plate 107 (FIGS. 4 and 5), and its absence from the turret will be noted by the inspector at the inspection station A. If such absence occurs repeatedly, the inspector can take such remedial action as may be needed.

18 Degrees to 38 Degrees

The cam lowers the cam follower 164 and spindle 150 to lower the chuck 36 and the vial 35 to an inspection position in which it is fully exposed for inspection and in which it stands directly above the output end of one of the optic fiber bundles 120 so as to be illuminated from below with intense light from that optic bundle.

38 Degrees to 103 Degrees—Inspection Station A

Over this length, the cam 170 is formed with a land 173 which maintains the cam follower 164 at a constant elevation and thereby holds the chuck 36 and vial 35 at a constant elevation for inspection. Meanwhile, the spinner cup 88 of the spindle assembly moves into engagement with the belt 250 which controls rotation of the spindles during their passage through this first inspection station A. Desirably, such belt is driven so as to cause the spindle and the vial 35 to rotate slowly as it travels across the inspection window 42 in view of the inspector. As indicated in FIG. 3, a continuous series of slowly rotating and continuously moving vials 35 are carried across the inspection window so that each and all may be inspected on a continuous and comparative or pattern basis for all of a variety of possible defects. Each vial is intensely lighted from below by a beam of light from one of the optic fiber bundles 102, and these move with the vials 35 so that each is illuminated from below by a substantially continuous and constant beam of intense light adapted to show up various defects and especially cracks in the glass vials. The vials are held by the top surfaces of their caps so that otherwise the vials are entirely exposed for observation, not only of the bottle portions but also of the stoppers and covers. If any defect appears, the inspector taps the defective vial with a finger to dislodge it from its chuck 36 and causes it to fall inward onto the reject-collection plate 107, as indicated in FIG. 4, where it is swept around on that plate by one of the spoke arms 104 of the light wheel and to the chute 112 leading to the reinspection conveyor 114.

103 Degrees to 123 Degrees

Over this length, the cam 170 is formed with a rise which causes the cam follower 164 to rise and lift the spindle 150 and its chuck so as to elevate the vial 35 into the spinner cup 88 to stabilize it for the next spinning step.

As the vials are lifted away from the light wheel, they pass over the support bar 134a for the light box 116 at the first inspection station A, which bar extends across the rim 100 of the light wheel at this point, as indicated at this position in FIG. 10 and shown in plan in FIG. 4.

123 Degrees to 195 Degrees

Over this length, the cam 170 is formed with a horizontal elevated land 175 along which the cam follower 164 travels at a constant elevation so that the vial 34 remains in the spinner cup 88. During this travel, spinner cup 88 is engaged with the spinner belt 260 which spins such cup and the vial 35 at high speed, say of 500 rpm, and this continues for a time sufficient to cause the liquid contents of the vial to attain a high-speed rotating movement.

When the vial contains components which require mixing, this spinning operation will produce the necessary mixing of such components, whether or not spinning is needed for inspection purposes.

At the end of this spin travel, and before the vials 35 are lowered to their subsequent inspection position, they pass over the support bar 134b for the light box 116 at the second inspection station B, which bar extends across the rim 100 of the light wheel carrying the optic fiber bundles 102, as indicated at this position in FIG. 10 and is shown in plan in FIG. 4.

195 Degrees to 217 Degrees

The cam 170 has a down slope to lower the cam follower 164 and the spindle 150 and the vial 35 to a lowered position for inspection at the second inspection station B. Also, the spinner cup 88 leaves the spinner belt 260, and the frictional drag on the spindle assembly causes the spindle assembly and the vial 35 to stop rotation, leaving the liquid contents of the vial with a continuing spinning motion.

217 Degrees to 282 Degrees

The cam follower traverses a land 177 on the cam 170. The vial 35 is carried through the second inspection station B with the bottle of the vial substantially stationary but with the contents of the vial continuing to spin as the result of the prior spinning step. This causes particles in the liquid contents to be lifted from the bottom of the vial and suspended in the spinning liquid where they may be observed under the intense lighting conditions prevailing. In some cases, observation of such particles may be enhanced by hanging a light-polarizing screen over the translucent panel 118 of the light box 116, by slipping it under the clips 124, so as to polarize the incident light in one plane, and by hanging a second polarizing sheet in the clips 128 on a support bar 126 (FIG. 5) with such polarizing sheet oriented to polarize the light in a different plane. The crossed planes of polarization substantially block the light transmitted from the light box 116 to the inspector so as to provide a dark background. Any light scattered by particles or defects in the vial 35 being observed will be depolarized and will show up in high contrast against the dark background.

282 Degrees to 303 Degrees

The cam 170 is here formed with a slight rise leading to a slightly elevated land 179 so that the cam follower 164 is elevated a short distance to lift the spindle 170 and the vial 35 carried on its chuck a slight distance sufficient to amply clear the bottom support plate 45 of the star wheel 43.

303 Degrees to 318 Degrees

The cam follower 164 moves along the elevated land 179, and carries the vial 35 into one of the vial-receiving pockets of the outfeed star wheel 44 in a slightly elevated position above the bottom support plate 45 of such star wheel. As the cam follower moves to the position D at 318 degrees where the pockets of the star wheel come into alignment with the axes of the chucks 35, the connected suction line 176 for the chuck leaves the vacuum chamber 180 and moves into communication with air pressure chamber 182 so as to be supplied with air under pressure therefrom. This breaks the vacuum which has held the vial 35 on the vacuum chuck 36 and causes the vial to be dropped from such chuck into the outfeed star wheel for delivery to the outfeed conveyor 46.

The inspection machine is constructed and adapted to facilitate a number of different inspection sequences. The inspection sequence described above is adapted for inspection of transparent vials containing transparent liquid contents, and the inspection includes: a first inspection at station A with the vials slowly rotated as they are carried in continuous sequence across the inspection window, a spinning step in which the vials are raised into stabilizing cups 88 and spun at high speed to cause their contents to attain a high rotative speed, and a second inspection at inspection station B with the vials substantially stationary but with their contents rotating so that foreign particles will be suspended for observation. In the case of vials which contain translucent but nontransparent suspensions, so that suspended particles will not be observable, the second inspection may be omitted. If mixing of vial contents is desired, the spinning step may be used for that purpose, whether or not used for inspection purposes. Various lighting conditions may be employed, as to eliminate or vary the intensity of the overhead lighting or the back lighting or the bottom lighting at either inspection station, and polarized or filtered lighting may be employed at either inspection station by mounting polarizing or filter screens over the translucent panel 118 of either light box 116 or under the clips 128, or at both such positions.

What is claimed is:

1. Apparatus for inspecting objects, such as medicinal vials and the like, having surfaces at their ends by which the objects may be gripped to expose their sides and opposite ends, comprising a series of chucks for gripping such objects at their said surfaces to carry them for inspection, and means to move such chucks to carry the objects along an inspection path in a continuously moving, closely spaced sequence across an inspection station at which a substantial number of objects are simultaneously exposed for inspection, means for feeding objects to said chucks ahead of said inspection station, means for illuminating each object with an individual beam of light directed toward the object and moving with the object as it traverses said inspection station, the number of continuously moving objects simultaneously exposed for inspection at said inspection station being sufficient to permit comparative or pattern inspection thereof during their travel across the inspection station.

2. Apparatus as in claim 1 in which said chucks carry the objects releasably so as to permit dislodgement thereof by an inspector at such station, and reject-receiving means disposed along the path of the objects at said inspection station, to which an inspector may dislodge defective objects from their chucks.

3. Apparatus as in claim 1 in which the objects have end faces adapted to make sealing engagement with chuck seal faces, and said chucks are vacuum chucks having seal faces for engagement with said object end faces, and means to supply vacuum to said chucks to actuate the same at said pickup position and continuously as the chucks carry objects through the inspection station.

4. Apparatus as in claim 1 in which the objects are containers such as medicinal vials and the like having end closures defining end surfaces adapted to be gripped by vacuum chucks, and said chucks are vacuum chucks engaging said surfaces for carrying said objects thereby with the other surfaces thereof exposed.

5. Apparatus as in claim 4 in which said objects are carried in depending position below the chucks.

6. Apparatus as in claim 1 or 5 in which said chucks are adapted to release an object carried thereby in response to finger pressure on the object by the inspector, and reject-receiving means in position to receive objects so released.

7. Apparatus as in claim 1 or 4 with the addition of means for slowly rotating the chucks substantially on the axes of the objects carried thereby as they traverse said inspection station.

8. Apparatus as in claim 7 in which the chucks are axially movable, and means for varying the axial positions of the chucks at different points along the inspection path.

9. Apparatus as in claim 1 or 4 with the addition of means for rapidly rotating the objects substantially on the axes of the chucks, and means for stabilizing the objects on the chucks during such rotation.

10. Apparatus as in claim 9 in which said stabilizing means comprises a generally cylindrical wall coaxial with the chuck, one being axially movable relative to the other to dispose the object carried by the chuck within and stabilized by the wall.

11. Apparatus as in claim 4 comprising first and second inspection stations across which objects are successively carried in a continuously moving closely spaced sequence,
said chucks being rotatable substantially on the axes of the objects carried thereby,
means for providing slow rotation of the objects during their travel across the first station,
means for rapidly rotating the chucks and objects carried thereby during their travel between said two inspection stations so as to generate spin in the contents of the objects,
such rapid rotation being discontinued as the objects enter the second station so as to leave such contents spinning during at least part of the inspection at said second inspection station.

12. Apparatus as in claim 11 in which the objects have end faces by which they are releasably carried, and said chucks are vacuum chucks which releasably carry the objects by such faces, further comprising spinner cups coaxial with said chucks and defining axially open cups of a size to closely surround the objects carried by the chucks, and means to move the chucks so as to dispose the objects carried thereby into said cups, the cups being rotated with the chucks and objects and being operative to stabilize the objects on the chucks during said rapid rotation thereof.

13. Apparatus as in claim 12 in which said means for rotating the chucks and objects comprises drive means engaging the external surfaces of said spinner cups during their travel to said second inspection station.

14. Apparatus as in claim 4, said chucks being rotatable substantially on the axes of the objects carried thereby, further comprising means for rapidly rotating the chucks and the objects carried thereby so as to generate spin in the contents of the objects so as to permit inspection for suspended particles therein, spinner cups coaxial with the chucks and defining downward open cups to closely surround the objects carried by the chucks, and means to move the chucks and cups axially relative to each other so as to dispose the objects within the cup, the cups being rotated with the chucks and objects and being operative to stabilize the objects on the chucks during rapid rotation thereof.

15. Apparatus as in claim 1 or 4 in which said illuminating means comprises a series of light-transmitting systems having their output ends disposed respectively toward and coaxially with said chucks, and movable therewith during the travel of said chucks across said inspection station, and light source means from which the input ends of said systems receive light during their movement with the chucks across said inspection station.

16. Apparatus as in claim 15 in which said chucks travel in a circular path across said inspection station, said light-transmitting systems are optic fiber bundles having their output ends mounted for revolution in a circular path opposite the path of the chucks, said optic fiber bundles extending inward toward the axis of said circular path and having their input ends in more closely spaced relation than their output ends, said light source means being concentrated adjacent such axis and the input ends of the bundles being arranged to travel across such light source.

17. Apparatus as in claim 4 in which said containers are translucent, and said illuminating means projects beams of light against the ends of the containers opposite from the ends gripped by the chucks.

18. Apparatus for inspecting objects, such as medicinal vials or the like which are generally symmetrical about a longitudinal axis and have an end portion by which the object may be carried to expose substantially their entire sides and opposite ends, comprising
spindle carrier means,
a series of spindles carried by said means for rotative and lengthwise movement on their axes,
chucks on said spindles for releasably carrying such objects coaxially with the spindles and along an inspection path in sequence across an inspection station,
means for feeding objects to said chucks,
a spinner cup about each spindle and rotatable therewith and defining an axially open cup of a size to closely surround a coaxial object carried by the chuck on the spindle, and means to move the spindle axially relative to the cup at at least one point in its travel through the inspection apparatus to carry the chuck and its object into the cup.

19. Apparatus as in claim 18 in which the chuck is moved into the cup between the object-feeding position and the inspection station to check the concentricity of the object on the chuck.

20. Apparatus as in claim 18 in which the chuck is moved into the cup at a spin position in advance of an inspection station, and means for rotating the cup and spindle at such spin station so as to generate spin in the contents of the object, said cup and spindle rotation being discontinued and the object stopped from rotation and moved out of the cup so as to expose the object with its contents spinning during at least part of the inspection at such station.

21. Apparatus as in claim 20 in which said rotating means drivingly engages the external surfaces of the cups.

22. Apparatus as in claim 18 or 20 with the addition of cam followers, said spindles being connected for rotation relative to, and for axial movement with, such cam followers, and cam means controlling the axial positions of said followers relative to the spinner cups as they travel through the inspection apparatus.

23. Apparatus as in claim 18 in which said spinner cups comprise inserts defining the object-receiving openings thereof, such inserts being replaceable to adapt the apparatus for the inspection of different sizes of objects.

24. Apparatus for inspecting objects, such as medicinal vials or the like, having portions at one end thereof by which the same may be supported to expose their sides and bottoms for inspection, comprising a turret having a peripheral series of a multiplicity of closely spaced chucks for releasably carrying a series of such objects in a generally circular path from an infeed position, across an inspection station and to an outfeed position, means for driving said turret in rotation, infeed means for feeding objects to said chucks at said infeed position, means to illuminate the exposed objects during their transverse of said inspection station, the objects exposed at said station being inspected from outside such circular path and being releasable from the chucks so as to dislodged therefrom by finger pressure, and reject-collection means along and inward of said path at said station to receive objects so dislodged.

25. Apparatus as in claim 24 in which said objects have end surfaces adapted to be gripped by vacuum chucks, and said chucks are vacuum chucks having seal faces for gripping the objects by such end surfaces and thereby carrying the objects through said circular path.

26. Apparatus as in claim 24 in which said illuminating means comprises means rotating with said turret and including means to project intense beams of light toward the objects traversing the inspection station and to move such beams with such objects during such traverse.

27. Apparatus as in claim 26 in which such light beam projecting means comprises a series of optic fiber bundles having their output ends fixed in said means rotating with the turret, and fixed light source means across which the input ends of such bundles move as their output ends traverse the inspection station.

28. Apparatus as in claim 24 in which said illuminating means comprises a light wheel rotatable with the turret and having a rim portion opposite the chucks on the turret, a plurality of light conductors having their output ends fixed in said light wheel rim opposite and aligned with said chucks for projecting beams of light against the ends of the objects carried by said chucks, and light source means radially inward of said rim portion, the light conductors extending inward and having their input ends arranged to traverse said light source as their output ends traverse the inspection station.

29. Apparatus as in claim 28, further comprising a reject collection plate inward of said rim portion of the light wheel, the light wheel being formed with spoke-like arms which sweep across said reject collection plate and discharge means to which such arms sweep rejected objects.

30. Apparatus as in claim 29 in which said light conductors extend through said sweep arms and said light source means is located radially inward of such sweep arms.

31. Apparatus as in claim 24 in which said reject collection means comprises a plate disposed inward of and below the circular path of the objects, and at least one sweep arm rotatable with the turret and movable across said plate to move rejected objects thereon to a discharge point, and means at such point for removing objects from said plate.

32. Apparatus as in any of claims 24, 25, 27, or 28 in which said objects have top end surfaces and said chuck seal faces are bottom seal faces for gripping the top end surfaces of the objects, the objects being carried through the inspection station in depending positions.

33. Apparatus as in claim 24, further comprising a series of spindles carrying said chucks and mounted on said turret for rotation on their axes, a cylindrical spinner cup rotatably mounted in the turret coaxially with each spindle, the spindle being connected for rotation with and axial movement relative to its spinner cup, and means to move the spindle axially at a predetermined position of the turret for moving into the cup the object carried by the chuck.

34. Apparatus for visually inspecting translucent objects, such as medicinal vials or the like, adapted to be carried along an inspection path past an inspection station, a turret continuously rotatable on an axis and having a circumferential series of closely spaced chucks for carrying a series of such objects in closely spaced relation along a generally circular path from an infeed position, across an inspection station at which several such objects are exposed for inspection, and to an outfeed position, a series of light-transmitting systems in fixed relationship with the turret and having their output ends disposed respectively to direct light onto the respective objects and so as to move continuously with and at the same speed as the turret and remain in substantially constant illuminating relation with the respective objects as they traverse the inspection station, stationary light source means adjacent the axis of the turret, said light-transmitting systems extending inward toward the axis of the turret and having their input ends disposed to receive light from said stationary source means as their output ends move with the several objects traversing the inspection station.

35. Apparatus as in claim 34 in which said light-transmitting means comprise light conductors fixed in a carrier continuously rotatable with the turret and directed toward the positions of objects carried by said chucks.

36. Apparatus as in claim 35 in which said light conductors are optic fiber bundles.

37. Apparatus as in claims 34 or 36 in which the objects are translucent containers which are gripped by their top closures and carried in depending positions on said turret, and said light-transmitting systems have their output ends positioned in a carrier rotatable with the turret and below the objects and project beams of light upward against the translucent bottom ends of the containers.

38. Apparatus for inspecting objects, such as medicinal vials or the like, which are generally symmetrical about longitudinal axes, comprising a turret rotatable on an axis and having a circumferential series of a multiplicity of closely spaced chucks for carrying a series of such objects coaxially with the chucks in a generally circular path from an infeed position across an inspection station, a series of spindles respectively carrying said chucks and mounted on the turret for rotation on their axes, means for driving said turret in continuous rotation, infeed means for feeding a series of objects to said chucks at said infeed position, means for rotating said spindles on their axes at a predetermined position along the path of the objects, said inspection station including means for simultaneously exposing a series of objects on said closely spaced chucks in sufficient number to permit comparative or pattern inspection thereof as they traverse the station, means to illuminate the exposed objects with substantially uniform illumination during such traverse, and a cylindrical spinner cap rotatably mounted on the turret coaxially with each spindle, the spindle being connected for rotation with and axial movement relative to its spinner cup, and means at a predetermined position of the turret to move the spindle and its chuck so as to dispose in such cup the object carried by the chuck.

39. Apparatus as in claim 38 in which the chuck and object is moved into the spinner cup between said infeed position and the inspection station for checking concentricity of the object relative to the axis of the chuck.

40. Apparatus as in claim 38 in which said objects are containers of liquid and said spindle-rotating means operates to rotate the spindles at a high speed in advance of the inspection station so as to create spin in the liquid contents of the containers, said rotation being discontinued and the spindles substantially stopped so as to leave the contents spinning during at least a portion of their traverse of the inspection station.

41. Apparatus as in claim 38 or 40 with the addition of cam followers connected to said spindles, a cam extending about the axis of the turret and followed by said followers to determine the axial positions of the spindles and chucks in their path of movement with the turret.

42. Apparatus as in claims 40, or 33 in which said turret carries objects on the chucks in a continuous path across said inspection station and also another inspection station.

43. Apparatus as in claim 42 in which the chucks and objects are rotated at high speed as they approach the second of said two inspection stations so as to create spin in the contents of the objects during at least a portion of their traverse of the second inspection station.

44. Apparatus for visually inspecting objects, such as medicinal vials or the like, which are generally symmetrical about longitudinal axes, comprising a turret rotatable on an axis and having a circumferential series of a multiplicity of closely spaced chucks for carrying a series of such objects coaxially with the chucks in a generally circular path from an infeed position across an inspection station, a series of spindles respectively carrying said chucks and mounted on the turret for rotation on their axes, means for driving said turret in continuous rotation, infeed means for feeding a series of objects to said chucks at said infeed position, means for rotating said spindles on their axes at a predetermined position along the path of the objects, said inspection station including means for simultaneously exposing a series of objects on said closely spaced chucks in sufficient number to permit visual comparative or pattern inspection thereof as they traverse the station, and means to illuminate the exposed objects with substantially uniform illumination during such traverse, wherein said illuminating means comprises a light wheel rotatable with the turret and including means adjacent its periphery to project beams of light against the objects carried by said chucks, and further including a light box mounted behind the path of objects across said inspection station, said chuck spindles being mounted for axial movement relative to the light wheel, means to move the spindles axially to move the chucks away from the light wheel at a predetermined position along said path, and support means for the light box extending therefrom outward across the periphery of the light wheel at such position so as to support the light box within the circular path of the objects.

45. Apparatus for inspecting objects, such as medicinal vials or the like, which are generally symmetrical about a longitudinal axis and have upper surfaces by which the same may be suspended to expose their sides and bottoms for inspection, comprising a turret having a peripheral series of spaced chucks for carrying a series of such objects in a generally circular path from an infeed position across an inspection station, an outer vertical cylindrical spinner mounted for rotation on the axis of each chuck and for revolution with the turret in a fixed axial position relative thereto, a spindle extending coaxially through said spinner and carrying a chuck at its lower end, the spindle being connected for rotation with the spinner and for axial movement relative thereto, a follower block connected to the spindle for controlling the axial position thereof, cam means extending along the path of movement of the follower blocks as they move with the turret and followed by the follower blocks for controlling the axial positions of the blocks and spindles, means for driving said turret in continuous rotation,
means to rotate the spinners during a portion of their revolution with the turret,
infeed means for feeding objects to said chucks at said infeed position, and
means to illuminate the objects during their traverse across the inspection station.

46. Apparatus as in claim 45 in which each spindle is biased upward relative to its spinner, said cam means comprises a cam plate above the spindles, and said follower blocks are mounted between the spindles and said cam plate so as to be held against the cam plate by the upward bias of the spindles.

47. Apparatus as in claim 45 in which the spindle and spinner assemblies include a downward open cup above the chuck on the spindle, of a size to closely surround an object carried by the chuck, said cam means being operative to lift the spindles to elevate the chuck and an object carried thereby into the cup to stabilize it substantially on the axis of the chuck, and said spinner rotation means rotates the spinner while the object is thus stabilized.

48. Apparatus as in claim 47 in which said spinner forms said cup.

49. Apparatus as in claim 45 in which said chucks are fluid pressure actuated chucks, each spindle having a fluid passage therethrough connected in sealed relation with a fluid passage in the follower block, and means to connect the block passage to a source of fluid pressure during a predetermined movement of the block with the turret.

50. Apparatus as in claim 49 in which said connection means comprises a fixed manifold, a valve block rotatable with the turret and over such fixed manifold, and a flexible line connecting each block passage to said valve block for connecting such passage to the manifold.

51. Apparatus as in claim 45 in which said objects are translucent, and illuminating means comprises a light wheel rotatable with the turret and having means for projecting beams of light upward against the bottoms of objects carried by said chucks as such objects traverse the inspection station.

52. Apparatus as in claim 45 in which said illuminating means comprises a light wheel rotatable with the turret and having a rim portion below the chucks on the turret, a plurality of light conductors having their output ends fixed in said light wheel rim below and aligned with said chucks for projecting beams of light against the bottoms of the objects carried by said chucks, and light source means radially inward of said rim portion, the optic fiber bundles extending inward and having their input ends positioned to traverse said light source as their output ends traverse the inspection station.

53. Apparatus as in claims 2, 14, 18, 24, or 45 in which the objects being inspected are medicinal vials or the like having top closures including a protective cap fixed in place by a frangible connection and adapted to be broken away by finger force of the user, and said chucks grip such caps with a force less than such break-away force so as to permit the objects to be dislodged from the chucks without breaking away the caps thereof.

54. Apparatus for inspecting objects, such as a medicinal container or the like, having portions at one end thereof by which the same may be supported for inspection, comprising
a turret having a peripheral series of a multiplicity of closely spaced chucks for releasably carrying a series of such objects in a generally circular path from an infeed position, across an inspection station and to an outfeed position,
means for driving said turret in rotation,
infeed means for feeding objects to said chucks at said infeed position,
means to illuminate the exposed objects during their traverse of said inspection station,
the objects exposed at said station being inspected from outside such circular path and being held releasably by the chucks so as to be removable manually therefrom as they traverse the inspection station, and reject-receiving means along said path at said station to receive objects so removed.

55. Apparatus for inspecting objects, such as medicinal vials or the like, which are generally symmetrical about longitudinal axes, comprising
a turret rotatable on an axis and having a circumferential series of chucks for carrying a series of such objects coaxially with the chucks in a generally circular path from an infeed position across an inspection station,
a series of spindles respectively carrying said chucks and mounted on the turret for rotation on their axes,
means for driving said turret in continuous rotation,
infeed means for feeding a series of objects to said chucks at said infeed position,
means for rotating said spindles on their axes at a predetermined position along the path of the objects,
said inspection station including means for exposing objects on said chucks for inspection thereof as they traverse the station,
means to illuminate the exposed objects during such traverse, and
a cylindrical spinner cup rotatably mounted on the turret coaxially with each spindle, the spindle being connected for rotation with and axial movement relative to its spinner cup, and means at a predetermined position of the turret to move the spindle and its chuck so as to dispose in such cup the object carried by the chuck.

56. Apparatus as in claim 55 in which the chuck and object is moved into the spinner cup between said infeed position and the inspection station for checking concentricity of the object relative to the axis of the chuck.

57. Apparatus as in claim 55 in which said objects are containers of liquid and said spindle-rotating means operates while such containers are disposed in the spinner cups to rotate the spindles at a high speed in advance of the inspection station so as to create spin in the liquid contents of the containers, said rotation being discontinued and the spindles substantially stopped and the containers disposed outside the spinner cups so as to present the containers with their contents spinning during at least a portion of their traverse of the inspection station.

* * * * *

UNITED STATES PATENT AND TRADEMARK OFFICE
CERTIFICATE OF CORRECTION

PATENT NO. : 4,417,662

DATED : November 29, 1983

INVENTOR(S) : David W. Nicholson et al

It is certified that error appears in the above-identified patent and that said Letters Patent is hereby corrected as shown below:

Column 10, line 5, change "of" to --in--.

Column 13, line 17, change "34" to --35--.

Column 19, line 42 (claim 38), change "cap" to --cup--.

Signed and Sealed this

Twenty-first Day of February 1984

[SEAL]

Attest:

GERALD J. MOSSINGHOFF

Attesting Officer

Commissioner of Patents and Trademarks